US008859705B2

(12) United States Patent
Lu et al.

(10) Patent No.: US 8,859,705 B2
(45) Date of Patent: Oct. 14, 2014

(54) HYDROGEL TISSUE ADHESIVE HAVING DECREASED GELATION TIME AND DECREASED DEGRADATION TIME

(71) Applicant: Actamax Surgical Materials, LLC, Berkeley, CA (US)

(72) Inventors: Helen S. M. Lu, Wallingford, PA (US); Cara L. Blankenbicker, Wilmington, DE (US)

(73) Assignee: Actamax Surgical Materials LLC, Berkeley, CA (US)

( * ) Notice: Subject to any disclaimer, the term of this patent is extended or adjusted under 35 U.S.C. 154(b) by 10 days.

(21) Appl. No.: 13/680,801

(22) Filed: Nov. 19, 2012

(65) Prior Publication Data

US 2014/0142063 A1    May 22, 2014

(51) Int. Cl.
 *A61K 47/36* (2006.01)
 *A61K 47/20* (2006.01)
 *A61K 31/715* (2006.01)

(52) U.S. Cl.
 CPC .............. *A61K 47/20* (2013.01); *A61K 31/715* (2013.01); *A61K 47/36* (2013.01)
 USPC .................. 527/305; 514/2; 514/59; 514/777

(58) Field of Classification Search
 None
 See application file for complete search history.

(56) References Cited

U.S. PATENT DOCUMENTS

| | | | |
|---|---|---|---|
| 4,542,176 A | 9/1985 | Graham | |
| 4,584,188 A | 4/1986 | Graham | |
| 4,703,116 A | 10/1987 | Solarek et al. | |
| 4,731,162 A | 3/1988 | Solarek et al. | |
| 4,741,804 A | 5/1988 | Solarek et al. | |
| 4,749,800 A | 6/1988 | Jobe et al. | |
| 4,766,245 A | 8/1988 | Larkin et al. | |
| 4,909,251 A | 3/1990 | Seelich | |
| 4,911,926 A | 3/1990 | Henry et al. | |
| 5,092,883 A | 3/1992 | Eppley et al. | |
| 5,116,824 A | 5/1992 | Miyata et al. | |
| 5,162,430 A | 11/1992 | Rhee et al. | |
| 5,196,441 A | 3/1993 | Kunisch et al. | |
| 5,217,485 A | 6/1993 | Liu et al. | |
| 5,275,838 A | 1/1994 | Merrill | |
| 5,292,802 A | 3/1994 | Rhee et al. | |
| 5,308,889 A | 5/1994 | Rhee et al. | |
| 5,324,775 A | 6/1994 | Rhee et al. | |
| 5,328,995 A | 7/1994 | Schaulin et al. | |
| 5,451,398 A | 9/1995 | Vigh | |
| 5,502,042 A | 3/1996 | Gruskin et al. | |
| 5,505,952 A | 4/1996 | Jiang et al. | |
| 5,514,379 A | 5/1996 | Weissleder et al. | |
| 5,567,685 A | 10/1996 | Linden et al. | |
| 5,643,575 A | 7/1997 | Martinez et al. | |
| 5,733,563 A | 3/1998 | Fortier | |
| 5,830,986 A | 11/1998 | Merrill et al. | |
| 5,840,698 A | 11/1998 | Campbell et al. | |
| 5,843,865 A | 12/1998 | Del Corral et al. | |
| 5,874,500 A | 2/1999 | Rhee et al. | |
| 6,051,648 A | 4/2000 | Rhee et al. | |
| 6,121,375 A | 9/2000 | Eknoian | |
| 6,150,472 A | 11/2000 | Engbers | |
| 6,165,488 A | 12/2000 | Tardy et al. | |
| 6,166,130 A | 12/2000 | Rhee et al. | |
| 6,323,278 B2 | 11/2001 | Rhee et al. | |
| 6,391,939 B2 | 5/2002 | Tayot et al. | |
| 6,410,519 B1 | 6/2002 | Gruskin et al. | |
| 6,458,147 B1 | 10/2002 | Cruise et al. | |
| 6,458,889 B1 | 10/2002 | Trollsas et al. | |
| 6,465,694 B1 | 10/2002 | Baudys et al. | |
| 6,514,534 B1 | 2/2003 | Sawhney | |
| 6,534,591 B2 | 3/2003 | Rhee et al. | |
| 6,602,952 B1 | 8/2003 | Bentley et al. | |
| 6,620,125 B1 | 9/2003 | Redl | |
| 6,664,102 B2 | 12/2003 | Illman et al. | |
| 6,689,399 B1 | 2/2004 | Dickson | |
| 6,696,089 B2 | 2/2004 | Kabanov et al. | |
| 6,703,047 B2 | 3/2004 | Sawhney et al. | |
| 6,743,521 B2 | 6/2004 | Hubbell et al. | |
| 6,756,518 B2 | 6/2004 | Gruskin et al. | |
| 6,800,278 B1 | 10/2004 | Perrault et al. | |
| 6,828,401 B2 | 12/2004 | Nho et al. | |

(Continued)

FOREIGN PATENT DOCUMENTS

| | | |
|---|---|---|
| EP | 0961783 | 1/2007 |
| JP | 1982-102932 | 6/1982 |

(Continued)

OTHER PUBLICATIONS

Thome, J., et al., "Ultrathin Antibacterial Polyammonium Coatings on Polymer Surfaces"; Surface and Coatings Technology, 174-175, 2003, pp. 584-587.
Harris, J. Milton, "Laboratory Synthesis of Polyethylene Glycol Derivatives", JMS—Rev., Macromol. Chem. Phys., C25 (3), 1985, pp. 325-373.
Harris, J. Milton, et al., "Synthesis of New Poly(Ethylene Glycol) Derivatives", PolyEthylene Glycol Chemistry: Biotechnical and Biomedical Applications, edited by Milton J. Harris, Plenum Press: New York, 1992, pp. 371-381.
Chen, Nicole, et al., "Mechanisms of Aldehyde-Containing Paper Wet-Strength Resins", Industrial & Engineering Chemistry Research, vol. 41, No. 22, 2002, pp. 5366-5371.
Callant, Dominique, et al., "A New Approach to Dextran Derivatives with Pendent Aldehyde Groups", Reactive Polymers, vol. 8, 1988, pp. 129-136.

(Continued)

*Primary Examiner* — James J Seidleck
*Assistant Examiner* — Peter A Salamon
(74) *Attorney, Agent, or Firm* — McCarter & English, LLP

(57) ABSTRACT

A hydrogel tissue adhesive having decreased gelation time and decreased degradation time is described. The hydrogel tissue adhesive is formed by reacting an oxidized polysaccharide containing aldehyde groups with a water-dispersible, multi-arm amine in the presence of a thiol additive. The thiol additive accelerates the process to form the hydrogel and accelerates the degradation of the hydrogel formed. The hydrogel may be useful as a tissue adhesive or sealant for medical applications, such as a hemostat sealant or to prevent undesired tissue-to-tissue adhesions resulting from trauma or surgery.

20 Claims, No Drawings

(56) References Cited

U.S. PATENT DOCUMENTS

| | | | |
|---|---|---|---|
| 6,833,408 B2 | 12/2004 | Schl et al. | |
| 6,844,028 B2 | 1/2005 | Mao et al. | |
| 6,858,736 B2 | 2/2005 | Nho et al. | |
| 6,896,725 B2 | 5/2005 | Thornton et al. | |
| 6,949,524 B2 | 9/2005 | Singh et al. | |
| 7,217,845 B2 | 5/2007 | Rosen et al. | |
| 7,323,539 B2 | 1/2008 | Sunkara et al. | |
| 7,347,850 B2 | 3/2008 | Sawhney | |
| 7,834,065 B2 | 11/2010 | Nakajima et al. | |
| 7,837,986 B2 | 11/2010 | Chenault | |
| 7,868,132 B2 | 1/2011 | Chenault | |
| 7,883,694 B2 | 2/2011 | Rhee et al. | |
| 7,960,498 B2 | 6/2011 | Chenault et al. | |
| 8,202,963 B2 | 6/2012 | Chenault et al. | |
| 8,241,609 B2 | 8/2012 | Figuly et al. | |
| 8,282,959 B2 | 10/2012 | Arthur et al. | |
| 8,426,492 B2 | 4/2013 | Lu | |
| 8,431,114 B2 | 4/2013 | Kodokian et al. | |
| 8,545,871 B2 * | 10/2013 | Arthur et al. | 424/443 |
| 2002/0146826 A1 | 10/2002 | Domb | |
| 2002/0151520 A1 | 10/2002 | Gruskin | |
| 2004/0086479 A1 | 5/2004 | Grinstaff et al. | |
| 2005/0002893 A1 | 1/2005 | Goldmann | |
| 2005/0288684 A1 | 12/2005 | Aronson et al. | |
| 2006/0193899 A1 | 8/2006 | Sawhney | |
| 2006/0292030 A1 | 12/2006 | Odermatt et al. | |
| 2007/0031467 A1 | 2/2007 | Abrahams et al. | |
| 2007/0048251 A1 | 3/2007 | Arthur | |
| 2008/0220047 A1 | 9/2008 | Sawhney et al. | |
| 2009/0035249 A1 | 2/2009 | Bhatia et al. | |
| 2010/0015231 A1 | 1/2010 | Lu | |
| 2010/0016886 A1 | 1/2010 | Lu | |
| 2010/0125155 A1 | 5/2010 | Arthur | |
| 2010/0160960 A1 | 6/2010 | Wagman et al. | |
| 2010/0297745 A1 * | 11/2010 | Li et al. | 435/287.2 |
| 2011/0224724 A1 * | 9/2011 | Lu et al. | 606/214 |
| 2011/0250257 A1 * | 10/2011 | Arthur et al. | 424/443 |
| 2012/0004194 A1 | 1/2012 | Lu et al. | |
| 2012/0035129 A1 | 2/2012 | Wagman | |
| 2012/0094955 A1 | 4/2012 | Wagman | |
| 2012/0142787 A1 | 6/2012 | Lu et al. | |
| 2012/0148523 A1 | 6/2012 | Lu et al. | |
| 2013/0035309 A1 | 2/2013 | Butterick et al. | |
| 2013/0189221 A1 | 7/2013 | Kodokian et al. | |

FOREIGN PATENT DOCUMENTS

| | | |
|---|---|---|
| JP | 1988-11167 | 1/1988 |
| WO | WO 87/00836 | 2/1987 |
| WO | WO 90/10441 | 9/1990 |
| WO | WO 91/15368 | 10/1991 |
| WO | WO 97/30103 | 8/1997 |
| WO | WO 99/01143 | 1/1999 |
| WO | WO 00/69925 | 11/2000 |
| WO | WO 01/49268 | 7/2001 |
| WO | WO 01/72280 | 10/2001 |
| WO | WO 01/87986 | 11/2001 |
| WO | WO 02/102864 | 12/2002 |
| WO | WO 03/020818 | 3/2003 |
| WO | WO 03/097759 | 11/2003 |
| WO | WO 2006/031358 | 3/2006 |
| WO | WO 2006/042161 | 4/2006 |
| WO | WO 2006/080523 | 8/2006 |
| WO | WO 2006/086510 | 8/2006 |
| WO | WO 2008/005207 | 1/2008 |
| WO | WO 2008/066787 | 6/2008 |
| WO | WO 2009/064977 | 5/2009 |
| WO | WO 2010/111570 | 9/2010 |
| WO | WO 2010/118284 | 10/2010 |

OTHER PUBLICATIONS

Hollander, Andreas, et al., "Polymer Surface Chemistry for Biologically Active Materials", Applied Surface Science, vol. 235, 2004, pp. 145-150.

Stone, H. Harlan, et al., "Antibiotic Prophylaxis in Gastric, Biliary and Colonic Surgery", Ann. Surg; Oct. 1976, pp. 443-450.

Fishman, Alexander, et al., "Synthesis and Investigation of Novel Branched PEG-Based Soluble Polymer Supports", The Journal of Organic Chemistry, vol. 68, 2003, pp. 9843-9846.

Newkome, George R., "Improved Synthesis of an Ethereal Tetraamine Core for Dendrimer Construction", The Journal of Organic Chemistry, vol. 67, 2002, pp. 3957-3960.

Halabi, A., et al., "Synthesis and Characterization of a Novel Dendritic Acrylic Monomer", The Journal of Organic Chemistry, vol. 65, 2000, pp. 9210-9213.

Harris, J. Milton, et al., "Synthesis and Characterization of Poly(ethylene Glycol) Derivatives", Journal of Polymer Science: Polymer Chemistry Edition, vol. 22, 1984, pp. 341-352.

Merrill, Edward W., "Poly(ethylene oxide) Star Molecules: Synthesis, Characterization, and Applications in Medicine and Biology", Journal of Biomaterials Science Polymer Edition, vol. 5, No. 1/2, 1993, pp. 1-11.

Zhao, Xuan, et al., "Novel Degradable Poly(ethylene glycol) Esters for Drug Delivery", Poly(ethylene glycol) Chemistry and Biological Applications, Oxford University Press, 1998, Chapter 28, pp. 458-472.

Azzam, Tony, et al., "Cationic Polysaccharides for Gene Delivery", Macromolecules, vol. 35, No. 27, 2002, pp. 9947-9953.

Nagasaki, Yukio, et al., "Formyl-Ended Heterobifunctional Poly(ethylene oxide): Synthesis of Poly(ethylene oxide) with a Formyl Group at One End and a Hydroxyl Group at the Other End", Bioconjugate Chemistry, vol. 6, No. 2, 1995, pp. 231-233.

Greenwald, Richard B., et al., "Drug Delivery Systems Employing 1,4- or 1,6-Elimination: Poly(ethylene glycol) Prodrugs of Amine-Containing Compounds", Journal of Medicinal Chemistry, vol. 42, No. 18, 1999, pp. 3657-3667.

Zalipsky, Samuel, et al., "Preparation and Applications of Polyethylene Glycol—Polystyrene Graft Resin Supports for Solid-Phase Peptide Synthesis", Reactive Polymers, vol. 22, 1994, pp. 243-258.

Lara, V.S., et al., "Dentin-Induced In Vivo Inflammatory Response and In Vitro Activation of Murine Macrophages", Journal of Dental Research, vol. 82, No. 6, 2003, pp. 460-465.

Atassi, M.Z., "Immunochemistry of Proteins", vol. 1, Plenum Press, New York, 1977, pp. 59-60.

Sweeney, Thomas, et al., "Intestinal Anastomoses Detected with a Photopolymerized Hydrogel", Surgery, vol. 131, No. 2, Feb. 2002, pp. 185-189.

Kim, Jae Chan, et al., "Evaluation of Tissue Adhesives in Closure of Scleral Tunnel Incisions", Journal of Cataract & Refractive Surgery, vol. 21, May 1995, pp. 320-325.

Sarayba, Melvin A., et al., "Inflow of Ocular Surface Fluid Through Clear Corneal Cataract Incisions: A Laboratory Model", American Journal of Ophthalmology, vol. 138, No. 2, Aug. 2004, pp. 206-210.

Buckmann, Andreas F., et al., "Functionalization of Poly(ethylene glycol) and Monomethoxy-Poly(ethylene glycol)", Makromolecular Chemistry, vol. 182, 1981, pp. 1379-1384.

Bruce, J., et al., "Systematic Review of the Definition and Measurement of Anastomotic Leak after Gastrointestinal Surgery", British Journal of Surgery, vol. 88, 2001, pp. 1157-1168.

Mo, Xiumei, et al., "Soft Tissue Adhesive Composed of Modified Gelatin and Polysaccharides", Journal of Biomaterials Science Polymer Edition, vol. 11, No. 4, 2000, pp. 341-351.

Hofreiter, B.T., et al., "Rapid Estimation of Dialdehyde Content of Periodate Oxystarch through Quantitative Alkali Consumption", Analytical Chemistry, vol. 27, No. 12, Dec. 1955, pp. 1930-1931.

Zhao, Huiru, et al., "Determination of Degree of Substitution of Formyl Groups in Polyaldehyde Dextran by the Hydroxylamine Hydrochloride Method", Pharmaceutical Research, vol. 8, No. 3, 1991, pp. 400-402.

Kurisawa, Motoichi, et al., "Double-Stimuli-Responsive Degradation of Hydrogels Consisting of Oligopeptide-Terminated Poly(ethylene glycol) and Dextran with an Interpenetrating Polymer Network", Journal of Biomaterials Science Polymer Edition, vol. 8, No. 9, 1997, pp. 691-708.

Pfannemuller, B., et al., "Chemical Modification of the Surface of the Starch Granules", Starch/Starke, vol. 95, No. 9, 1983, pp. 298-303.

(56) References Cited

OTHER PUBLICATIONS

Ahmad, Shavej, et al., "Dextran and 5-aminosalicylic Acid (5-ASA) Conjugates: Synthesis, Characterisation and Enzymic Hydrolysis", Carbohydrate Research, vol. 341, 2006, pp. 2694-2701.

Cortesi, Rita, et al., "Dextran Cross-linked Gelatin Microspheres as a Drug Delivery System", European Journal of Pharmaceutics and Biopharmaceutics, vol. 47, 1999, pp. 153-160.

Gill, Inderbir S., et al., "Improved Hemostasis During Laparoscopic Partial Nephrectomy Using Gelatin Matrix Thrombin Sealant", Adult Urology, vol. 64, No. 3, 2005, pp. 463-466.

BASF Corp, Technical Bulletin, Pluronic F108 Block Copolymer Surfactant, (2004), 1 Page.

Yao, Zhong, et al, A Series of Novel Chitosan Derivatives: Synthesis, Characterization and Micellar Solubilization of Paclitaxel, Carbohydrate Polymers, vol. 68, 2007, pp. 781-792.

* cited by examiner

HYDROGEL TISSUE ADHESIVE HAVING DECREASED GELATION TIME AND DECREASED DEGRADATION TIME

FIELD OF THE INVENTION

The invention relates to the field of medical adhesives. More specifically, the invention relates to a hydrogel tissue adhesive formed by reacting an oxidized polysaccharide containing aldehyde groups with a water-dispersible, multi-arm amine in the presence of a thiol additive. The thiol additive decreases the gelation time to form the hydrogel and also decreases the degradation time of the resulting hydrogel.

BACKGROUND OF THE INVENTION

Tissue adhesives have many potential medical applications, including wound closure, supplementing or replacing sutures or staples in internal surgical procedures, adhesion of synthetic onlays or inlays to the cornea, drug delivery devices, and as anti-adhesion barriers to prevent post-surgical adhesions. Conventional tissue adhesives are generally not suitable for a wide range of adhesive applications. For example, cyanoacrylate-based adhesives have been used for topical wound closure, but the release of toxic degradation products limits their use for internal applications. Fibrin-based adhesives are slow curing, have poor mechanical strength, and pose a risk of viral infection. Additionally, fibrin-based adhesives do not covalently bind to the underlying tissue.

Several types of hydrogel tissue adhesives have been developed, which have improved adhesive and cohesive properties and are nontoxic (see for example Sehl et al., U.S. Patent Application Publication No. 2003/0119985 A1, and Goldmann, U.S. Patent Application Publication No. 2005/0002893 A1). These hydrogels are generally formed by reacting a component having nucleophilic groups with a component having electrophilic groups, which are capable of reacting with the nucleophilic groups of the first component, to form a crosslinked network via covalent bonding. However, these hydrogels typically swell or dissolve away too quickly, or lack sufficient adhesion or mechanical strength, thereby decreasing their effectiveness as surgical adhesives.

Kodokian et al. (copending and commonly owned U.S. Patent Application Publication No. 2006/0078536 A1) describes hydrogel tissue adhesives formed by reacting an oxidized polysaccharide with a water-dispersible, multi-arm polyether amine. These adhesives provide improved adhesion and cohesion properties, crosslink readily at body temperature, maintain dimensional stability initially, do not degrade rapidly, and are nontoxic to cells and non-inflammatory to tissue. However, for certain applications, a hydrogel tissue adhesive that forms more rapidly and degrades more rapidly is desired. For example, for use as a tissue adhesive or hemostat in a liver resection, rapid gelation is required to minimize blood loss and the hydrogel should degrade in a timely manner to prevent an inflammatory reaction. Additionally, if the hydrogel-forming precursors are delivered to a tissue surface using a spray device, rapid gelation is required so that the hydrogel forms in the desired location. The gelation rate can be increased by increasing the concentration of the reactive groups of the hydrogel precursors, but this leads to a hydrogel with a higher crosslink density which consequently degrades more slowly.

Figuly et al. (copending and commonly owned U.S. Patent Application Publication No. 2010/0112063 A1) describes the use of certain chemical additives which increase the gelation time to form a hydrogel tissue adhesive and decrease the degradation time of the resulting hydrogel.

Wagman et al. (copending and commonly owned U.S. Patent Application Publication No. 2010/0160960 A1) describes the use of a polyol additive to increase the degradation time of a hydrogel tissue adhesive.

Wagman et al. (copending and commonly owned U.S. Patent Application Publication No. 2012/0035129 A1) describes the use of an oligomer additive to decrease the degradation time of a hydrogel tissue adhesive, but the gelation time to form the hydrogel is not decreased.

In view of the above, a need exits for a hydrogel tissue adhesive which has an increased rate of gelation and an increased degradation rate.

SUMMARY OF THE INVENTION

In various embodiments, provided herein is a hydrogel tissue adhesive, formed by reacting an oxidized polysaccharide containing aldehyde groups with a water-dispersible, multi-arm amine, in the presence of a thiol additive which decreases the gelation time to form the hydrogel and also decreases the degradation time of the resulting hydrogel.

One embodiment provides a kit for forming a hydrogel, the kit comprising:
a) a first aqueous solution or dispersion comprising:
   (i) at least one oxidized polysaccharide containing aldehyde groups, having a weight-average molecular weight of about 1,000 to about 1,000,000 Daltons and having an equivalent weight per aldehyde group of about 65 to about 1,500 Daltons, said first aqueous solution or dispersion containing from about 5% to about 40% by weight of the oxidized polysaccharide; and
   (ii) at least one thiol additive, wherein the thiol additive is water-dispersible, contains only one reactive thiol (SH) group, does not contain any reactive carboxylic acid, primary amine or secondary amine groups, and has a molecular weight in the range of about 60 Daltons to about 40,000 Daltons, said first aqueous solution or dispersion containing about 0.1% to about 20% by weight of the thiol additive; and
b) a second aqueous solution or dispersion comprising at least one water-dispersible, multi-arm amine wherein at least three of the arms are terminated by at least one primary amine group, said multi-arm amine having a number-average molecular weight of about 440 to about 200,000 Daltons, said second aqueous solution or dispersion containing from about 5% to about 70% by weight of the multi-arm amine; or
c) a water-dispersible, multi-arm amine in the form of a neat liquid wherein at least three of the arms are terminated by a primary amine group, wherein said at least one multi-arm amine has a number-average molecular weight of about 440 to about 200,000 Daltons.

Another embodiment provides a hydrogel comprising the reaction product of:
a) a first aqueous solution or dispersion comprising:
   (i) at least one oxidized polysaccharide containing aldehyde groups, having a weight-average molecular weight of about 1,000 to about 1,000,000 Daltons and having an equivalent weight per aldehyde group of about 65 to about 1,500 Daltons, said first aqueous solution or dispersion containing from about 5% to about 40% by weight of the oxidized polysaccharide; and (ii) at least one thiol additive, wherein the thiol additive is water-dispersible, contains only one reactive thiol (SH) group, does not contain any reactive carboxylic acid, primary amine or secondary amine groups, and has a molecular weight in the range of about 60 Daltons to about 40,000 Daltons, said first aqueous solution or dispersion containing about 0.1% to about 20% by weight of the thiol additive; and b) a second aqueous solution or dispersion comprising at least one water-dispersible, multi-arm amine wherein at least three of the arms are terminated by at least one primary amine group, said multi-arm amine having a number-average molecular weight of about 440 to about 200,000 Daltons, said second aqueous solution or dispersion containing from about 5% to about 70% by weight of the multi-arm polyether amine; or c) a water-dispersible, multi-arm amine in the form of a neat liquid wherein at least three of the arms are terminated by a primary amine group, wherein said at least one multi-arm amine has a number-average molecular weight of about 440 to about 200,000 Daltons.

Another embodiment provides a method for applying a coating to an anatomical site on tissue of a living organism comprising:
applying to the site a) a first aqueous solution or dispersion comprising:
(i) at least one oxidized polysaccharide containing aldehyde groups, having a weight-average molecular weight of about 1,000 to about 1,000,000 Daltons and having an equivalent weight per aldehyde group of about 65 to about 1,500 Daltons, said first aqueous solution or dispersion containing from about 5% to about 40% by weight of the oxidized polysaccharide; and (ii) at least one thiol additive, wherein the thiol additive is water-dispersible, contains only one reactive thiol (SH) group, does not contain any reactive carboxylic acid, primary amine or secondary amine groups, and has a molecular weight in the range of about 60 Daltons to about 40,000 Daltons, said first aqueous solution or dispersion containing about 0.1% to about 20% by weight of the thiol additive; and b) a second aqueous solution or dispersion comprising at least one water-dispersible, multi-arm amine wherein at least three of the arms are terminated by at least one primary amine group, said multi-arm amine having a number-average molecular weight of about 440 to about 200,000 Daltons, said second aqueous solution or dispersion containing from about 5% to about 70% by weight of the multi-arm amine; or c) a water-dispersible, multi-arm amine in the form of a neat liquid wherein at least three of the arms are terminated by a primary amine group, wherein said at least one multi-arm amine has a number-average molecular weight of about 440 to about 200,000 Daltons;

wherein (a) and (b) or (c) are applied to the site in any order, or (a) and (b) or (c) are premixed and the resulting mixture is applied to the site before the mixture completely cures.

DETAILED DESCRIPTION

As used above and throughout the description of the invention, the following terms, unless otherwise indicated, shall be defined as follows:

The term "oxidized polysaccharide" refers to a polysaccharide which has been reacted with an oxidizing agent to introduce aldehyde groups into the molecule. Oxidation of the polysaccharide rings results in dialdehydes formed by opening the rings of the polysaccharide.

The term "equivalent weight per aldehyde group" refers to the molecular weight of the oxidized polysaccharide divided by the number of aldehyde groups introduced in the molecule.

The term "water-dispersible, multi-arm amine" refers to a polymer having three or more polymer chains ("arms"), which may be linear or branched, emanating from a central structure, which may be a single atom, a core molecule, or a polymer backbone, wherein at least three branches ("arms") are terminated by at least one primary amine group. The water-dispersible, multi-arm amine is water soluble or is able to be dispersed in water to form a colloidal suspension capable of reacting with a second reactant in aqueous solution or dispersion.

The term "water-dispersible, multi-arm polyether amine" refers to a branched polyether, wherein at least three of the branches ("arms") are terminated by at least one primary amine group, which is water soluble or able to be dispersed in water to form a colloidal dispersion capable of reacting with a second reactant in aqueous solution or dispersion.

The term "polyether" refers to a polymer having the repeat unit [–O—R]—, wherein R is a hydrocarbyl group having 2 to 5 carbon atoms. The polyether may also be a random or block copolymer comprising different repeat units.

The term "branched polyether" refers to a polyether having one or more branch points ("arms"), including star, dendritic, comb, and hyperbranched polyethers.

The term "dendritic polyether" refers to a highly branched polyether having a tree-like structure.

The term "comb polyether" refers to a polyether having a main chain with multiple trifunctional branch points from each of which a linear arm emanates.

The term "star polyether" refers to a polyether having a central branch point, which may be a single atom or a chemical group, from which linear arms emanate.

The term "hyperbranched polyether" refers to a highly branched polyether having fewer branches and less regular branching than a dendritic polyether.

The term "thiol additive" refers to a water-dispersible, chemical compound that contains only one reactive thiol (SH) group, does not contain any reactive carboxylic acid, primary amine or secondary amine groups, and has a molecular weight in the range of about 60 Daltons to about 40,000 Daltons.

The term "reactive thiol (SH) group" refers to a thiol group on the additive that is capable of reacting with an aldehyde group on the oxidized polysaccharide, and that may induce crosslinking of oxidized polysaccharides.

The term "reactive carboxylic acid (i.e. —COOH), primary amine or secondary amine groups" refer to any carboxylic acid, primary amine or secondary amine groups on the additive that are capable of reacting with an aldehyde group on the oxidized polysaccharide, and that may induce crosslinking of oxidized polysaccharides.

The term "water-dispersible" as used herein in reference to the thiol additive described herein, refers to a thiol additive that is water soluble or able to be dispersed in water to form a colloidal dispersion.

The term "primary amine" refers to a neutral amino group having two free hydrogens. The amino group may be bound to a primary, secondary or tertiary carbon.

The term "secondary amine" refers to a neutral amino group having one free hydrogen. The amino group may be bound to a primary, secondary or tertiary carbon.

The term "multi-functional amine" refers to a chemical compound comprising at least two functional groups, at least one of which is a primary amine group.

The term "crosslink" refers to a bond or chain of atoms attached between and linking two different polymer chains.

The term "crosslink density" is herein defined as the reciprocal of the average number of chain atoms between crosslink connection sites.

The term "% by weight", also referred to herein as "wt %" refers to the weight percent relative to the total weight of the solution or dispersion, unless otherwise specified.

The term "anatomical site" refers to any external or internal part of the body of humans or animals.

The term "tissue" refers to any biological tissue, both living and dead, in humans or animals.

The term "hydrogel" refers to a water-swellable polymeric matrix, consisting of a three-dimensional network of macromolecules held together by covalent crosslinks that can absorb a substantial amount of water to form an elastic gel.

The term "PEG" as used herein refers to poly(ethylene glycol).

The term "$M_w$" as used herein refers to the weight-average molecular weight.

The term "$M_n$" as used herein refers to the number-average molecular weight.

The term "medical application" refers to medical applications as related to humans and animals.

Where a range of values is provided, it is understood that each intervening value between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

Disclosed herein is a hydrogel tissue adhesive that is formed by reacting an oxidized polysaccharide containing aldehyde groups with a water-dispersible, multi-arm amine in the presence of a thiol additive. The thiol additive decreases the gelation time to form the hydrogel and also decreases the degradation time of the resulting hydrogel. Also provided herein is a method for applying a coating to an anatomical site on tissue of a living organism with the hydrogel tissue adhesive disclosed herein.

Oxidized Polysaccharides

Oxidized polysaccharides useful in the invention include, but are not limited to, oxidized derivatives of: dextran, carboxymethyldextran, starch, agar, cellulose, hydroxyethylcellulose, carboxymethylcellulose, pullulan, inulin, levan, and hyaluronic acid. The starting polysaccharides are available commercially from sources such as Sigma Chemical Co. (St. Louis, Mo.). Typically, polysaccharides are a heterogeneous mixture having a distribution of different molecular weights, and are characterized by an average molecular weight, for example, the weight-average molecular weight ($M_w$), or the number average molecular weight ($M_n$), as is known in the art. Suitable oxidized polysaccharides have a weight-average molecular weight of about 1,000 to about 1,000,000 Daltons, more particularly about 3,000 to about 250,000 Daltons, more particularly about 5,000 to about 100,000 Daltons, and more particularly about 10,000 to about 60,000 Daltons. In one embodiment, the oxidized polysaccharide is oxidized dextran, also referred to herein as dextran aldehyde.

Oxidized polysaccharides may be prepared by oxidizing a polysaccharide to introduce aldehyde groups using any suitable oxidizing agent, including but not limited to, periodates, hypochlorites, ozone, peroxides, hydroperoxides, persulfates, and percarbonates. For example, the polysaccharide may be oxidized by reaction with sodium periodate as described by Mo et al. (*J. Biomater. Sci. Polymer Edn.* 11:341-351, 2000). The polysaccharide may be reacted with different amounts of periodate to give polysaccharides with different degrees of oxidation and therefore, different amounts of aldehyde groups. Additionally, the oxidized polysaccharide may be prepared using the method described by Cohen et al. (copending and commonly owned International Patent Application Publication No. WO 2008/133847 A1). That method of making an oxidized polysaccharide comprises a combination of precipitation and separation steps to purify the oxidized polysaccharide formed by oxidation of the polysaccharide with periodate, as described in detail in the Examples herein below, and provides an oxidized polysaccharide with very low levels of iodine-containing species. Alternatively, the method the oxidized polysaccharide may be prepared using the method described by Adelman et al. (copending and commonly owned International Patent Application Publication No. WO 2012/012359 A1).

The degree of oxidation, also referred to herein as the oxidation conversion, of the oxidized polysaccharide may be determined using methods known in the art. For example, the degree of oxidation of the oxidized polysaccharide may be determined using the method described by Hofreiter et al. (*Anal Chem.* 27:1930-1931, 1955). In that method, the amount of alkali consumed per mole of dialdehyde in the oxidized polysaccharide, under specific reaction conditions, is determined by a pH titration. Alternatively, the degree of oxidation of the oxidized polysaccharide may be determined using nuclear magnetic resonance (NMR) spectroscopy, as described in detail in the Examples herein below. In one embodiment, the equivalent weight per aldehyde group of the oxidized polysaccharide is from about 65 to about 1,500 Daltons, more particularly from about 90 to about 1,500 Daltons.

The oxidized polysaccharide is used in the form of an aqueous solution or dispersion, referred to herein as the first aqueous solution or dispersion. To prepare the first aqueous solution or dispersion, the oxidized polysaccharide is added to water to give a concentration of about 5% to about 40%, more particularly from about 5% to about 30%, and more particularly from about 15% to about 30% by weight relative to the total weight of the solution or dispersion. The optimal concentration to be used depends on the application and on the concentration of the multi-arm amine used, as described infra, and can be readily determined by one skilled in the art using routine experimentation. Additionally, a mixture of at least two different oxidized polysaccharides, having different polysaccharide backbones, different weight-average molecular weights, and/or different equivalent weights, may be used. Where a mixture of oxidized polysaccharides is used, the total concentration of the oxidized polysaccharides is about 5% to about 40%, more particularly from about 5% to about 30%, and more particularly from about 15% to about 30% by weight relative to the total weight of the solution or dispersion.

For use on living tissue, it is preferred that the first aqueous solution or dispersion be sterilized to prevent infection. Any suitable sterilization method known in the art that does not degrade the polysaccharide may be used, including, but not limited to, electron beam irradiation, gamma irradiation, ethylene oxide sterilization, or ultra-filtration through a 0.2 µm pore membrane.

The first aqueous solution or dispersion may further comprise various adjuvants depending on the intended application. Preferably, the adjuvant is compatible with the oxidized polysaccharide. Specifically, the adjuvant does not contain primary or secondary amine groups that would interfere with effective gelation to form a hydrogel. The amount of the adjuvant used depends on the particular application and may be readily determined by one skilled in the art using routine experimentation. For example, the first aqueous solution or may optionally include at least one thickener. The thickener may be selected from among known viscosity modifiers, including, but not limited to, polysaccharides and derivatives thereof, such as starch or hydroxyethyl cellulose.

The first aqueous solution or dispersion may optionally include at least one antimicrobial agent. Suitable antimicrobial preservatives are well known in the art. Examples of suitable antimicrobials include, but are not limited to, alkyl parabens, such as methylparaben, ethylparaben, propylparaben, and butylparaben; triclosan; chlorhexidine; cresol; chlorocresol; hydroquinone; sodium benzoate; and potassium benzoate.

The first aqueous solution or dispersion may also optionally include at least one colorant to enhance the visibility of the solution or dispersion. Suitable colorants include dyes, pigments, and natural coloring agents. Examples of suitable colorants include, but are not limited to, FD&C Violet No. 2, FD&C Blue No. 1, D&C Green No. 6, D&C Green No. 5, D&C Violet No. 2; and natural colorants such as beetroot red, canthaxanthin, chlorophyll, eosin, saffron, and carmine.

The first aqueous solution or dispersion may also optionally include at least one surfactant. Surfactant, as used herein, refers to a compound that lowers the surface tension of water. The surfactant may be an ionic surfactant, such as sodium lauryl sulfate, or a neutral surfactant, such as polyoxyethylene sorbitan monolaurate or polyethylene glycol tert-octyl-phenyl ether.

Additionally, the first aqueous solution or dispersion may optionally include a pharmaceutical drug or therapeutic agent, including but not limited to, antibacterial agents, antiviral agents, antifungal agents, anti-cancer agents, vaccines, radiolabels, anti-inflammatory agents, such as indomethacin, salicylic acid acetate, ibuprophen, sulindac, piroxicam, and naproxen; thrombogenic agents, such as thrombin, fibrinogen, homocysteine, and estramustine; and radio-opaque compounds, such as barium sulfate and gold particles.

Water-Dispersible, Multi-Arm Amines:

Suitable water-dispersible, multi-arm amines include, but are not limited to, water-dispersible multi-arm polyether amines, amino-terminated dendritic polyamidoamines, and multi-arm branched end amines. Typically, multi-arm amines suitable for use herein have a number-average molecular weight of about 440 to about 200,000 Daltons, more particularly from about 2,000 to about 40,000 Daltons.

In one embodiment, the water-dispersible, multi-arm amine is a multi-arm polyether amine, which is a water-dispersible polyether having the repeat unit [—O—R]—, wherein R is a hydrocarbylene group having 2 to 5 carbon atoms. Suitable multi-arm polyether amines include, but are not limited to, amino-terminated star polyethylene oxides, amino-terminated dendritic polyethylene oxides, amino-terminated comb polyethylene oxides, amino-terminated star polypropylene oxides, amino-terminated dendritic polypropylene oxides, amino-terminated comb polypropylene oxides, amino-terminated star polyethylene oxide-polypropylene oxide copolymers, amino-terminated dendritic polyethylene oxide-polypropylene oxide copolymers, amino-terminated comb polyethylene oxide-polypropylene oxide copolymers, and polyoxyalkylene triamines, sold under the trade name Jeffamine® triamines, by Huntsman LLC. (Houston, Tex.). Examples of star polyethylene oxide amines, include, but are not limited to, various multi-arm polyethylene glycol amines, and star polyethylene glycols having 3, 4, 6, or 8 arms terminated with primary amines (referred to herein as 3, 4, 6, or 8-arm star PEG amines, respectively). Examples of suitable Jeffamine® triamines include, but are not limited to, Jeffamine® T-403 (CAS No. 39423-51-3), Jeffamine® T-3000 (CAS No. 64852-22-8), and Jeffamine® T-5000 (CAS No. 64852-22-8). In one embodiment, the water-dispersible multi-arm polyether amine is an eight-arm polyethylene glycol having eight arms terminated by a primary amine group and having a number-average molecular weight of about 10,000 Daltons. In another embodiment, the water-dispersible multi-arm polyether amine is a mixture comprising an eight-arm polyethylene glycol having eight arms terminated by a primary amine group and having a number-average molecular weight of about 10,000 Daltons a four-arm polyethylene glycol having four arms terminated by a primary amine group and having a number-average molecular weight of about 2,000 Daltons.

The multi-arm polyether amines are either available commercially, as noted above, or may be prepared using methods known in the art. For example, multi-arm polyethylene glycols, wherein at least three of the arms are terminated by a primary amine group, may be prepared by putting amine ends on multi-arm polyethylene glycols (e.g., 3, 4, 6, and 8-arm star polyethylene glycols, available from companies such as Nektar Transforming Therapeutics; SunBio, Inc., Anyang City, South Korea; NOF Corp., Tokyo, Japan; or JenKem Technology USA, Allen, Tex.) using the method described by Buckmann et al. (*Makromol. Chem.* 182:1379-1384, 1981). In that method, the multi-arm polyethylene glycol is reacted with thionyl bromide to convert the hydroxyl groups to bromines, which are then converted to amines by reaction with ammonia at 100° C. The method is broadly applicable to the preparation of other multi-arm polyether amines. Additionally, multi-arm polyether amines may be prepared from multi-arm polyols using the method described by Chenault (copending and commonly owned U.S. Pat. No. 7,868,132). In that method, the multi-arm polyether is reacted with thionyl chloride to convert the hydroxyl groups to chlorine groups, which are then converted to amines by reaction with aqueous or anhydrous ammonia. Other methods that may be used for preparing multi-arm polyether amines are described by Merrill et al. in U.S. Pat. No. 5,830,986, and by Chang et al. in WO 97/30103 A1.

Water-dispersible, multi-arm amines suitable for use herein may also be amino-terminated dendritic polyamidoamines, sold under the trade name Starburst® Dendrimers (available from Sigma-Aldrich, St Louis, Mo.).

In one embodiment, the water-dispersible, multi-arm amine is a multi-arm branched end amine, as described by Arthur (copending and commonly owned U.S. Patent Application Publication No. 2010/0086678 A1). The multi-arm branched end amines are branched polymers having two or three primary amine groups at the end of each of the polymer arms. The multiplicity of functional groups increases the statistical probability of reaction at a given chain end and allows more efficient incorporation of the branched molecules into a polymer network. The starting materials used to prepare the branched end amines may be branched polymers such as multi-arm polyether polyols including, but not limited to, comb and star polyether polyols. The branched end amines can be prepared by attaching multiple amine groups to the ends of the polymer by reaction with the hydroxyl groups using methods well known in the art. For example, a branched end amine having two amine functional groups on each end of the polymer arms can be prepared by reacting the starting material, as listed above, with thionyl chloride in a suitable solvent such as toluene to give the chloride derivative, which is subsequently reacted with tris(2-aminoethyl)amine to give the branched end reactant having two primary amine groups at the end of the polymer arms.

It should be recognized that the water-dispersible, multi-arm amines are generally a somewhat heterogeneous mixture having a distribution of arm lengths and in some cases, a distribution of species with different numbers of arms. When a multi-arm amine has a distribution of species having different numbers of arms, it can be referred to based on the average number of arms in the distribution. For example, in one embodiment the multi-arm amine is an 8-arm star PEG amine, which comprises a mixture of multi-arm star PEG amines, some having less than and some having more than 8 arms; however, the multi-arm star PEG amines in the mixture have an average of 8 arms. Therefore, the terms "8-arm", "6-arm", "4-arm" and "3-arm" as used herein to refer to multi-arm amines, should be construed as referring to a heterogeneous mixture having a distribution of arm lengths and in some cases, a distribution of species with different numbers of arms, in which case the number of arms recited refers to the average number of arms in the mixture.

For use as disclosed herein, the multi-arm amine is typically used in the form of an aqueous solution or dispersion. However, the multi-arm amine need not be used in the form of an aqueous solution or dispersion. The presence of water is optional. For example, some multi-arm amines are liquids, which may be used neat.

In one embodiment, at least one multi-arm amine is used in the form of an aqueous solution or dispersion, referred to herein as the second aqueous solution or dispersion. The multi-arm amine is added to water to give a concentration of about 5% to about 70% by weight, more particularly from about 20% to about 50% by weight relative to the total weight of the solution or dispersion. The optimal concentration to be used depends on the application and on the concentration of the oxidized polysaccharide used in the first aqueous solution or dispersion. Additionally, a mixture of different multi-arm amines, having different backbones, different number-average molecular weights, and/or different numbers of arms, may be used. Where a mixture of multi-arm amines is used, the total concentration of the multi-arm amines is about 5% to about 70% by weight, more particularly from about 20% to about 50% by weight relative to the total weight of the solution or dispersion.

In one embodiment, the concentrations of the oxidized polysaccharide and the multi-arm amine are adjusted such that the aldehyde groups on the oxidized polysaccharide are in stoichiometric excess relative to the amine groups on the multi-arm amine.

For use on living tissue, it is preferred that the second aqueous solution or dispersion comprising the multi-arm amine be sterilized to prevent infection. Any of the methods described above for sterilizing the first aqueous solution or dispersion solution may be used.

The second aqueous solution or dispersion comprising the multi-arm amine may further comprise various adjuvants. Any of the adjuvants described above for the first aqueous solution or dispersion solution may be used. Additionally, the solution may comprise a healing promoter, such as chitosan.

Additionally, the second aqueous solution or dispersion may optionally comprise at least one other multi-functional amine having one or more primary amine groups to provide other beneficial properties, such as hydrophobicity or modified crosslink density. The multi-functional amine is capable of inducing gelation when mixed with an oxidized polysaccharide in an aqueous solution or dispersion. The multi-functional amine may be a second water dispersible, multi-arm amine, such as those described above, or another type of multi-functional amine, including, but not limited to, linear and branched diamines, such as diaminoalkanes, polyaminoalkanes, and spermine; linear branched end amines as described above, branched polyamines, such as polyethylenimine; cyclic diamines, such as N,N'-bis(3-aminopropyl)piperazine, 5-amino-1,3,3-trimethylcyclohexanemethylamine, 1,3-bis(aminomethyl)cyclohexane, 1,4-diaminocyclohexane, and p-xylylenediamine; aminoalkyltrialkoxysilanes, such as 3-aminopropyltrimethoxysilane and 3-aminopropyltriethoxysilane; aminoalkyldialkoxyalkylsilanes, such as 3-aminopropyldiethoxymethylsilane, dihydrazides, such as adipic dihydrazide; linear polymeric diamines, such as linear polyethylenimine, α, ω-amino-terminated polyethers, α, ω-bis(3-aminopropyl)polybutanediol, β, ω-1-amino-terminated polyethers (linear Jeffamines®); comb polyamines, such as chitosan, polyallylamine, and polylysine, and di- and polyhydrazides, such as bis(carboxyhydrazido)polyethers and poly(carboxyhydrazido) star polyethers. Many of these compounds are commercially available from companies such as Sigma-Aldrich and Huntsman LLC. Typically, if present, the multi-functional amine is used at a concentration of about 5% by weight to about 1000% by weight relative to the weight of the multi-arm amine in the second aqueous solution or dispersion.

In another embodiment, the multi-functional amine is provided in a separate solution at a concentration of about 5% by weight to about 100% by weight relative to the total weight of the solution. If the multi-functional amine is not used neat (i.e., 100% by weight), it is used in the form of an aqueous solution or dispersion. For use on living tissue, it is preferred that the solution comprising the multi-functional amine be sterilized. Any of the methods described above for sterilizing the first aqueous solution or dispersion may be used. The aqueous solution or dispersion comprising the multi-functional amine may further comprise various adjuvants. Any of the adjuvants described above for the first aqueous solution or dispersion or the second aqueous solution or dispersion solution may be used.

Thiol Additives

Suitable thiol additives for use in the hydrogels disclosed herein are water-dispersible, contains only one reactive thiol (SH) group, does not contain any reactive carboxylic acid, primary amine or secondary amine groups, and have a molecular weight in the range of about 60 Daltons to about 40,000 Daltons. Examples of suitable thiol additives include, but are not limited to, thioglycerol, mercaptoethanol, methyl thioglycolate, ethyl thioglycolate, 2-(2-methoxyethoxy) ethane thiol, salts of 2-mercaptoethane sulfonate, 4-hydroxy thiophenol, mercaptothiadiazole, mercaptobenzothiazole, and (2-mercaptoethyl)-guanidine sulfate. These thiol compounds may be obtained from commercial sources such as Sigma-Aldrich (Milwaukee, Wis.). Other suitable thiol additives include PEG molecules having a single active thiol group (e.g. 100-20,000 Da), for example, methoxy-PEG-$(CH_2)_2$—SH, molecular weight 20,000 Da. The chemical name is α-mercaptoethyl-ω-methoxy, polyoxyethylene, CAS#134874-49, available from NOF America Corp., White Plains, N.Y.

In some embodiments, the thiol additive is selected from the group consisting of: thioglycerol, methyl thioglycolate, 2-(2-methoxyethoxy) ethane thiol, and salts of 2-mercaptoethane sulfonate, such as sodium or potassium 2-mercaptoethane sulfonate.

In order to decrease the gelation time to form the hydrogel and to decrease the degradation time of the formed hydrogel, at least one thiol additive is added to the first aqueous solution or dispersion comprising the oxidized polysaccharide. The thiol additive is added to the aqueous solution or dispersion at a concentration of about 0.1% to about 20%, more particularly about 1% to about 20%, more particularly about 0.5% to about 10%, more particularly about 1% to about 10%, more particularly about 2% to about 10%, and more particularly about 1% to about 6% by weight relative to the weight of the aqueous solution or dispersion. If thiol additives are used, the total concentration of the additives in the aqueous solution or dispersion is about 0.1% to about 20%, more particularly about 1% to about 20%, more particularly about 0.5% to about 10%, more particularly about 1% to about 10%, more particularly about 2% to about 10%, and more particularly about 1% to about 6% by weight relative to the weight of the aqueous solution or dispersion. The amount of thiol additive(s) required to provide the desired reduction in gelation time and/or degradation time can be determined using routine experimentation. The effect of the thiol additive may be enhanced by combining the first aqueous solution or dispersion comprising the oxidized polysaccharide with the thiol additive and stored for a period of at least one hour, preferably at least 2 hours and more preferably at least six hours before use. The first aqueous solution or dispersion thiol additive combination may be stored at room temperature or at lower temperatures, e.g., at 4° C. in a refrigerator. Higher temperatures, e.g. 40° C., may be used which would decrease the storage time prior to use. Higher temperatures, however, also reduce the stability of the oxidized polysaccharide.

In one embodiment, the addition of the thiol additive in the first aqueous solution or dispersion is sufficient to provide at least about a 10% decrease in gelation time to form the hydrogel, under predetermined conditions as compared to that of a hydrogel formed under the same conditions, but in the absence of the thiol additive. For any set of predetermined conditions, the gelation time to form the hydrogel can be measured by a variety of different methods. For example, the first aqueous solution or dispersion comprising the oxidized polysaccharide and the thiol additive, and the second aqueous solution or dispersion comprising the multi-arm amine can be combined with stirring and the time it takes for the mixture to gel to the point where it holds its shape without flowing can be measured, as described in the Examples herein below. A more precise measurement of gelation time may be performed by oscillating disk rheometry. The gel point is the time at which the values of G' (the elastic or storage modulus) and G" (the viscous or loss modulus) are equal.

In another embodiment, the addition of the thiol additive in the first aqueous solution or dispersion is sufficient to provide at least about a 10% decrease in degradation time, under predetermined conditions as compared to that of a hydrogel formed under the same conditions, but in the absence of the thiol additive. For any set of predetermined conditions, the degradation time of the resulting hydrogel can be determined using methods known in the art. For example, after the hydrogel is formed, it can be incubated in an aqueous medium with shaking at a specified temperature and agitation speed and the time required for the hydrogel to dissolve can be measured, as described in the Examples herein below.

In some embodiments, the first aqueous solution or dispersion comprising the oxidized polysaccharide containing aldehyde groups and the thiol additive, and the second aqueous solution or dispersion comprising the multi-arm amine, may be used to apply a coating to an anatomical site on tissue of a living organism. The two aqueous solutions or dispersions may be applied to the site in any number of ways. Once both solutions or dispersions are combined on a site, they crosslink to form a hydrogel, a process referred to herein as curing. The hydrogel provides a coating on the site.

In some embodiments, the two aqueous solutions or dispersions are applied to the site sequentially using any suitable means including, but not limited to, spraying, brushing with a cotton swab or brush, or extrusion using a pipette, or a syringe. The solutions or dispersions may be applied in any order. Then, the solutions or dispersions are mixed on the site using any suitable device, such as a cotton swab, a spatula, or the tip of the pipette or syringe.

In some embodiments, the two aqueous solutions or dispersions are mixed manually before application to the site. The resulting mixture is then applied to the site before it completely cures using a suitable applicator, as described above.

In some embodiments, the first aqueous solution or dispersion and the second aqueous solution or dispersion are applied to the site simultaneously where they mix to form a hydrogel. For example, the two aqueous solutions or dispersions may be contained in separate barrels of a double-barrel syringe. In this way the two aqueous solutions or dispersions are applied simultaneously to the site with the syringe. Suitable double-barrel syringe applicators are known in the art. For example, Redl describes several suitable applicators for use as described herein in U.S. Pat. No. 6,620,125 (particularly FIGS. 1, 5, and 6, which are described in Columns 4, line 10 through column 6, line 47). The two aqueous solutions or dispersions may also be applied to the site using a dual-lumen catheter, such as those available from Bistech, Inc. (Woburn, Mass.). Additionally, injection devices for introducing two liquid components endoscopically into the body simultaneously are known in the art and may be adapted for the delivery of the two aqueous solutions or dispersions disclosed herein (see for example, Linder et al., U.S. Pat. No. 5,322,510).

In another embodiment, the first aqueous solution or dispersion and the second aqueous solution or dispersion may be premixed and delivered to the site using a double barrel syringe containing a motionless mixer, such as that available from ConProtec, Inc. (Salem, N.H.) or Mixpac Systems AG (Rotkreuz, Switzerland). Alternatively, the mixing tip may be equipped with a spray head, such as that described by Cruise et al. in U.S. Pat. No. 6,458,147. Additionally, the mixture of the two aqueous solutions or dispersions from the double-barrel syringe may be applied to the site using a catheter or endoscope. Devices for mixing a two liquid component tissue adhesive and delivering the resulting mixture endoscopically are known in the art and may be adapted for the mixing and delivery of the two aqueous solutions or dispersions disclosed herein (see for example, Nielson, U.S. Pat. No. 6,723,067; and Redl et al., U.S. Pat. No. 4,631,055).

In another embodiment, the two aqueous solutions or dispersions may be applied to the site using a spray device, such as those described by Fukunaga et al. (U.S. Pat. No. 5,582,596), Delmotte et al. (U.S. Pat. No. 5,989,215) or Sawhney (U.S. Pat. No. 6,179,862).

In another embodiment, the two aqueous solutions or dispersions may be applied to the site using a minimally invasive surgical applicator, such as those described by Sawhney (U.S. Pat. No. 7,347,850).

In another embodiment, the hydrogel tissue adhesive disclosed herein may be used to bond at least two anatomical sites together. In this embodiment, the first aqueous solution or dispersion is applied to at least one anatomical site, and the second aqueous solution or dispersion is applied to at least one of either the same site or one other site using the methods described above. The two or more sites are contacted and held together manually or using some other means, such as a surgical clamp, for a time sufficient for the mixture to cure. Alternatively, a mixture of the two aqueous solutions or dispersions is applied to at least one of the anatomical sites to be bonded using methods described above. The two or more sites are contacted and held together manually or using some other means, such as a surgical clamp, for a time sufficient for the mixture to cure.

Kits

In one embodiment, provided herein is a kit comprising a first aqueous solution or dispersion comprising at least one oxidized polysaccharide containing aldehyde groups and at least one thiol additive, and a second aqueous solution comprising at least one multi-arm amine, as described above. Each of the aqueous solutions or dispersions may be contained in any suitable vessel, such as a vial or a syringe barrel.

Medical Applications:

The hydrogel disclosed herein may be useful as a tissue adhesive or sealant for medical applications, including but not limited to, use as a hemostat sealant or to prevent undesired tissue-to-tissue adhesions resulting from trauma or surgery. In these applications, the first aqueous solution or dispersion comprising the oxidized polysaccharide and the thiol additive, and the second aqueous solution or dispersion comprising the water-dispersible multi-arm amine, may be applied to the desired anatomical site using the methods described above.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

The meaning of abbreviations used is as follows: the designation "10K" means that a polymer molecule possesses a weight-average molecular weight of 10 kiloDaltons, "min" means minute(s), "h" means hour(s), "sec" means second(s), "mL" means milliliter(s), "mol" means mole(s), "mmol" means millimole(s), "g" means gram(s), "mg" means milligram(s), "EW" means equivalent weight, "MW" means molecular weight, "wt %" means percent by weight, "mol %" means mole percent, "Vol" means volume, "v/v" means volume per volume, "PEG" means polyethylene glycol, "Da" means Daltons, "kDa" means kiloDaltons, "MWCO" means molecular weight cut-off, "Pa" means pascal(s), "kPa" means kilopascal(s), "MPa" means megapascal(s), $^1$H NMR" means proton nuclear magnetic resonance spectroscopy, "ppm" means parts per million, "D" means density in g/mL, "PBS" means phosphate-buffered saline, and "rpm" means revolutions per minute.

A reference to "Aldrich" or a reference to "Sigma" means the said chemical or ingredient was obtained from Sigma-Aldrich, St. Louis, Mo. A reference to "NOF" means the said chemical or ingredient was obtained from NOF Corp, Tokyo, Japan. A reference to "TCI America" means the said chemical or ingredient was obtained from TCI America, Portland, Oreg.

REAGENT PREPARATION

Preparation of Oxidized Dextran (D10-50)

Dextran aldehyde was made by oxidizing dextran having a weight-average molecular weight of 8,500 to 11,500 Daltons (Sigma) in aqueous solution with sodium metaperiodate. The oxidized dextran, referred to herein as D10-50, had an average molecular weight of about 10,000 Da and an oxidation conversion of about 50% (i.e., about half of the glucose rings in the dextran polymer are oxidized to dialdehydes). The oxidation conversion of the oxidized dextran was determined by proton NMR to be about 50% (equivalent weight per aldehyde group=146). In the NMR method, the integrals for two ranges of peaks are determined, specifically, —O$_2$CHx- at about 6.2 parts per million (ppm) to about 4.15 ppm (minus the HOD peak) and —OCHx- at about 4.15 ppm to about 2.8 ppm (minus any methanol peak if present). The calculation of oxidation level is based on the calculated ratio (R) for these areas, specifically, R=(OCH)/(O$_2$CH).

Preparation of Eight-Arm PEG 10K Octaamine (P8-10-1)

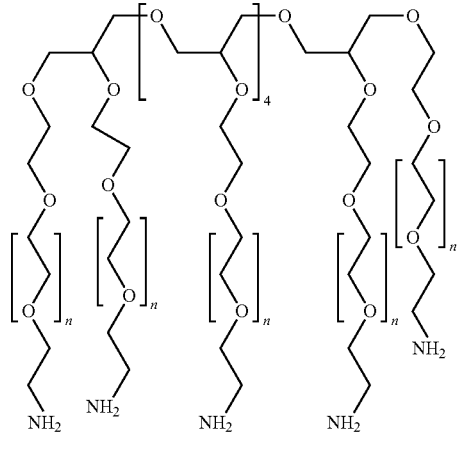

n=~25
P8-10-1 PEG Amine

Eight-arm PEG 10K octaamine (M$_n$=10 kDa) was synthesized using the two-step procedure described by Chenault in U.S. Pat. No. 7,868,132. In the first step, an 8-arm PEG 10K chloride was made by reaction of thionyl chloride with an 8-arm PEG 10K octaalcohol. In the second step, the 8-arm PEG 10K chloride was reacted with aqueous ammonia to yield the 8-arm PEG 10K octaamine. A typical procedure is described here.

The 8-arm PEG 10K octaalcohol (M$_n$=10000; NOF SunBright HGEO-10000), (100 g in a 500-mL round-bottom flask) was dried either by heating with stirring at 85° C. under vacuum (0.06 mm of mercury (8.0 Pa)) for 4 hours or by azeotropic distillation with 50 g of toluene under reduced pressure (2 kPa) with a pot temperature of 60° C. The 8-arm PEG 10K octaalcohol was allowed to cool to room temperature and thionyl chloride (35 mL, 0.48 mol) was added to the flask, which was equipped with a reflux condenser, and the mixture was heated at 85° C. with stirring under a blanket of nitrogen for 24 hours. Excess thionyl chloride was removed by rotary evaporation (bath temp 40° C.). Two successive 50-mL portions of toluene were added and evaporated under reduced pressure (2 kPa, bath temperature 60° C.) to complete the removal of thionyl chloride. Proton NMR results from one synthesis are:

$^1$H NMR (500 MHz, DMSO-d6) δ 3.71-3.69 (m, 16H), 3.67-3.65 (m, 16H), 3.50 (s, ~800H).

The 8-arm PEG 10K octachloride (100 g) was dissolved in 640 mL of concentrated aqueous ammonia (28 wt %) and heated in a pressure vessel at 60° C. for 48 hours. The solution was sparged for 1-2 hours with dry nitrogen to drive off 50 to 70 g of ammonia. The solution was then passed through a column (500 mL bed volume) of strongly basic anion exchange resin (PUROLITE® A-860, The Purolite Co., Bala-Cynwyd, Pa.) in the hydroxide form. The eluant was collected and three 250-mL portions of deionized water were passed through the column and also collected. The aqueous solutions were combined, concentrated under reduced pressure (2 kPa, bath temperature 60° C.) to about 200 g, frozen in portions and lyophilized to give the 8-arm PEG 10K octaamine, referred to herein as P8-10-1, as a colorless waxy solid.

Preparation of Four-Arm PEG 2K Tetraamine
(P4-2-1)

A 4-arm PEG 2K ($M_n$=2 kDa) tetraamine is prepared using a similar procedure as described above for the 8-arm PEG 10K octaamine.

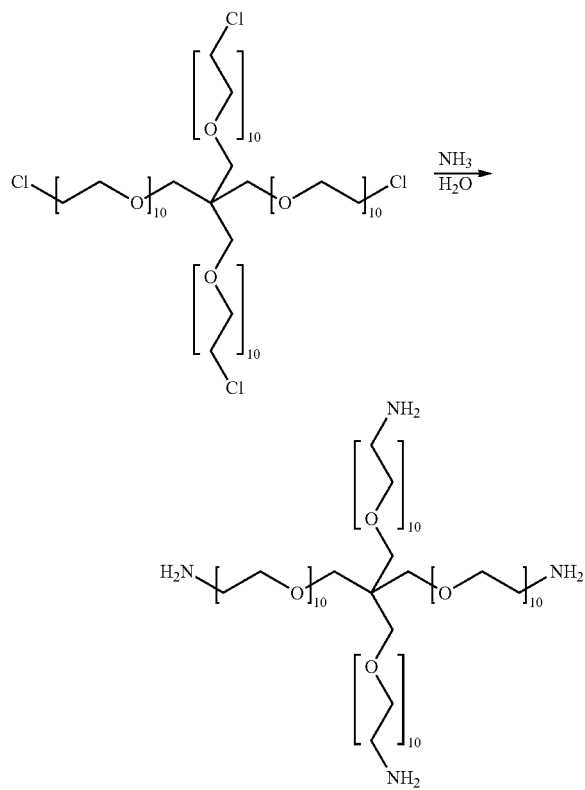

4-Arm PEG 2K Tetraamine

Four-arm PEG 2K tetraalcohol ($M_n$=2000; NOF SunBright PTE-2000), (100 g in a 500-mL round-bottom flask) is dissolved in 100 mL of dichloromethane. Thionyl chloride (88 mL, 1.2 mol) is added, and the mixture is stirred under a blanket of nitrogen at ambient temperature for 24 hours. Excess thionyl chloride and dichloromethane are removed by rotary evaporation (bath temp 40° C.). Two successive 50-mL portions of toluene are added and evaporated under reduced pressure (2 kPa, bath temperature 60° C.) to complete the removal of thionyl chloride.

Proton NMR results from one preparation are:

$^1$H NMR (500 MHz, DMSO-d6): δ 3.71-3.68 (m, 8H), 3.67-3.65 (m, 8H), 3.57-3.55 (m, 8H), 3.50 (m, ~140H), 3.47-3.45 (m, 8H), 3.31 (s, 8H).

The 4-arm PEG 2K tetrachloride (40 g) is dissolved in 600 mL of concentrated aqueous ammonia (28 wt %) and heated in a pressure vessel at 60° C. for 48 hours. The solution is cooled and sparged for 1.5 hours with dry nitrogen, and then concentrated by rotary evaporation (2 kPa, bath temperature 60° C.) to about 500 g. The solution is then passed through a column (500 mL bed volume) of strongly basic anion exchange resin (Purolite® A-860) in the hydroxide form. The eluant is collected, and two 250-mL portions of de-ionized water are passed through the column and collected. The aqueous fractions are combined and evaporated under reduced pressure (2 kPa, bath temperature 60° C.) to give the 4-arm PEG 2K tetraamine, referred to herein as P4-2-1, as a clear, pale-yellow liquid.

$^1$H NMR (500 MHz, CDCl$_3$): δ 3.65-3.51 (m, ~170H), 3.47 (m, 8H), 3.36 (s, 8H), 2.86 (t, J=5.3 Hz, 7.4H), 2.76 (t, J=5.4 Hz, 0.6H).

Examples 1-15

Hydrogels Having Decreased Gelation Time

The purpose of these Examples was to demonstrate the decreased gelation time of a hydrogel formed by reacting dextran aldehyde with a mixture of an 8-arm PEG amine (P8-10-1) and a 4-arm PEG amine (P4-2-1) using different thiol additives.

Varying amounts of thiol additives (obtained from Sigma-Aldrich), as shown in Table 1, were added to 10 g of an aqueous dextran aldehyde solution (D10-50, prepared as described in General Methods; 12 wt % solution) and the resulting solution was allowed to remain overnight at room temperature. The PEG amine solution was prepared by combining a 30 wt % aqueous solution of an 8-arm PEG amine ($M_n$=10,000, prepared as described in General Methods), and a 30 wt % aqueous solution of a 4-arm PEG amine ($M_n$=2000, prepared as described in General Methods) in a volume ratio of 9:1.

The next day, the gelation time for formation of the hydrogel from the dextran aldehyde and PEG amine solutions was measured by combining 0.1 mL of the dextran aldehyde solution containing the thiol additive and 0.1 mL of the PEG amine solution and mixing with a wooden rod until the mixture gelled to the point where the hydrogel held its own shape without flowing. This time was measured and taken as the gelation time. The results are shown in Table 1.

For comparison, the thiol additive was added to the PEG amine solution. In these studies, the dextran aldehyde and PEG amine solutions were prepared as described above. The thioglycerol was added to the PEG amine solution and the resulting solution was allowed to remain overnight at room temperature. The results are shown in Table 2.

TABLE 1

Effect of Thiol Additives on Gelation Times of Hydrogels
Formed by Reacting a Dextran Aldehyde Solution with a
PEG Amine Solution - Thiol Additive in Dextran Aldehyde
Solution

| Example | Thiol Additive | Weight of Thiol Added to 10 g of Dextran Aldehyde solution | Gelation Time (sec) |
|---|---|---|---|
| 1, Comparative | None | 0 | 10 |
| 2 | thioglycerol | 0.10 | 4 |
| 3 | thioglycerol | 0.21 | 4 |
| 4 | thioglycerol | 0.40 | 4 |
| 5 | methyl thioglycolate | 0.10 | 3 |
| 6 | methyl thioglycolate | 0.21 | 2 |
| 7 | methyl thioglycolate | 0.39 | 1 |
| 8 | 2-(2-methoxyethoxy)ethane thiol | 0.12 | 7 |
| 9 | 2-(2-methoxyethoxy)ethane thiol | 0.27 | 4 |
| 10 | 2-(2-methoxyethoxy)ethane thiol | 0.50 | 3 |
| 11 | sodium 2-mercaptoethane-sulfonate | 0.30 | 5 |
| 12 | sodium 2-mercaptoethane-sulfonate | 0.603 | 5 |

These results demonstrate that the addition of the thiols significantly decreased the gelation time to form hydrogels compared to the hydrogel formed without the thiol additive (Example 1, Comparative).
The gelation time of the hydrogel was decreased by over 90% at the highest methyl thioglycolate concentration used (Example 7).

TABLE 2

Effect of Thiol Additives on Gelation Times of Hydrogels
Formed by Reacting a Dextran Aldehyde Solution with a
PEG Amine Solution - Thiol Additive in PEG Amine Solution

| Example | Thiol Additive | Weight of Thiol Added to 10 g of PEG Amine solution | Gelation Time (sec) |
|---|---|---|---|
| 1, Comparative | None | 0 | 10 |
| 13, Comparative | thioglycerol | 0.10 | 9 to 10 |
| 14, Comparative | thioglycerol | 0.21 | 9 to 10 |
| 15, Comparative | thioglycerol | 0.40 | 9 |

The results shown in Table 2 demonstrate that the addition of the thiol additive to the PEG amine solution does not decrease the gelation time to form the hydrogel.

Example 16

Effect of Incubation Time of Thiol Additive in Dextran Aldehyde Solution

The purpose of this Example was to demonstrate the effect of incubation time of the thiol additive in the dextran aldehyde solution on the gelation time of a hydrogel formed by reacting dextran aldehyde with a mixture of an 8-arm PEG amine (P8-10-1) and a 4-arm PEG amine (P4-2-1) using different thiol additives.

The reagents were prepared as described above (Examples 1-15). The thiol additive was added to the dextran aldehyde solution and the resulting solution was incubated for a specified amount of time at room temperature or at 37° C., after which time the dextran aldehyde solution was mixed with PEG amine solution and the gel times were determined. The results are shown in Tables 3 and 4, respectively.

TABLE 3

Effect of Incubation Time of the Thiol Additives in the
Dextran Aldehyde Solution at Room Temperature on
the Gelation Times of Hydrogels Formed by Reacting
a Dextran Aldehyde Solution with a PEG Amine Solution

| Thiol Additive | Weight of Thiol Added to 10 g of Dextran Aldehyde solution (g) | Gel time (sec) T = 0 | Gel time after 1 h incubation | Gel time after 2 h incubation | Gel time after 4 h incubation |
|---|---|---|---|---|---|
| None | 0 | 9 | NA | NA | NA |
| thioglycerol | 0.21 | 6 | 5 | 4 | 4 |
| methyl thioglycolate | 0.10 | 8 | 7 | 2 | 3 |
| 2-(2-methoxyethoxy)ethane thiol | 0.27 | 8 | 7 | 6 | 4 |
| sodium 2-mercapto-ethane-sulfonate | 0.30 | 7 | 5 | 3 | 5 |

The results shown in Table 3 demonstrate that the effect of the thiol additive on the gelation time was dependent on the incubation time in the dextran aldehyde solution. The gelation time decreased as the incubation time of the thiol additive in the dextran aldehyde solution was increased. After an incubation time of 2 hours, the gelation time was significantly reduced.

TABLE 4

Effect of Incubation Time of the Thiol Additives in the
Dextran Aldehyde Solution at 37° C. on the Gelation
Times of Hydrogels Formed by Reacting a Dextran
Aldehyde Solution with a PEG Amine Solution

| Thiol Additive | Weight of Thiol Added to 10 g of Dextran Aldehyde solution (g) | Gel Time (sec) T = 0 | Gel time after 30 min incubation | Gel time after 1 h incubation |
|---|---|---|---|---|
| None | 0 | 9 | NA | NA |
| thioglycerol | 0.21 | 6 | 4 | 4 |
| Methyl thioglycolate | 0.10 | 8 | 5 | 3 |
| sodium 2-mercaptoethane-sulfonate | 0.30 | 7 | 5 | 4 |

When the thiol additive was incubated in the dextran aldehyde solution at elevated temperature (37° C.), the decrease in the gelation times was observed at even shorter incubation times, i.e., 30 min.

Examples 17-21

Hydrogels Having an Increased Rate of Hydrolytic Degradation

The purpose of these Examples was to demonstrate the increased rate of hydrolytic degradation of hydrogels due to thiol additives.

Hydrogel samples were prepared by mixing equal volumes of a 17 wt % aqueous solution of D10-50 dextran aldehyde containing a thiol additive (see Table 5), which was allowed to remain overnight at room temperature, and a 30 wt % aqueous solution of P8-10-1. After the hydrogels cured, they were weighed and placed inside glass vials containing PBS at pH 7.4. The vials were placed inside a temperature-controlled shaker set at 80 rpm and 37° C. The hydrogel samples were removed from the vials at various times, blotted to remove excess solution, and weighed. Then, the samples were returned to the vials.

The results are summarized in Table 5. The percent swell reported in the table is the weight of the hydrogel at the specified time divided by the initial weight of the hydrogel, multiplied by 100. The results demonstrate that the thiol-containing hydrogels (Examples 18-21) degraded more rapidly than the hydrogels without the thiol additive (Example 17, Comparative).

TABLE 5

Effect of Thiol Additives on the Degradation of Hydrogels

| Example | Thiol Additive | Mol Ratio Thiol:Ald | % Swell 6 h | 24 h | 384 to 432 h |
|---|---|---|---|---|---|
| 17, Comparative | none | 0 | 310 | 381 | 410 (432 h) |
| 18 | thioglycerol | 0.05 | 491 | 494 | 243 (384 h) |
| 19 | thioglycerol | 0.10 | 425 | 381 | 166 (384 h) |
| 20 | methyl thioglycolate | 0.05 | 464 | 500 | 209 (384 h) |
| 21 | methyl thioglycolate | 0.10 | 471 | 492 | 209 (384 h) |

Examples 22-27

Hydrogels Having an Increased Rate of Hydrolytic Degradation

The purpose of these Examples was to demonstrate the increased rate of hydrolytic degradation of hydrogels due to thiol additives.

Hydrogel samples were prepared by mixing equal volumes of a 12 wt % aqueous solution of D10-50 dextran aldehyde containing a thiol additive (see Table 6), which was allowed to remain overnight at room temperature, and an aqueous solution containing a mixture of P8-10-1 and P4-2-1 (9:1 volume ratio) at 30 wt %. After the hydrogels cured, they were weighed and placed inside glass vials containing PBS at pH 7.4. The vials were placed inside a temperature-controlled shaker set at 80 rpm and 37° C. The hydrogel samples were removed from the vials at various times, blotted to remove excess solution, and weighed. Then, the samples were returned to the vials.

The results are summarized in Table 6. The percent swell reported in the table is the weight of the hydrogel at the specified time divided by the initial weight of the hydrogel, multiplied by 100. The results demonstrate that the thiol-containing hydrogels (Examples 23-27) degraded more rapidly than the hydrogels without the thiol additive (Example 22, Comparative).

TABLE 6

Effect of Thiol Additives on the Degradation of Hydrogels

| Example | Thiol Additive | Mol Ratio Thiol:Ald | % Swell 6 h | 24 h | 48 h |
|---|---|---|---|---|---|
| 22, Comparative | none | 0 | 370 | 370 | 370 |
| 23 | thioglycerol | 0.06 | 474 | 72 | 47 |
| 24 | thioglycerol | 0.13 | 567 | 0 | 0 |
| 25 | methyl thioglycolate | 0.07 | 418 | 110 | 0 |
| 26 | methyl thioglycolate | 0.15 | 322 | 0 | 0 |
| 27 | 2-(2-methoxy-ethoxy)ethane thiol | 0.06 | 402 | 0 | 0 |

Examples 28-29

In-Vitro Burst Testing of a Sealed Scalpel Incision

The purpose of these Examples was to demonstrate the burst strength of a seal made with various hydrogels containing thiol additives of an incision made in the uterine horn from a pig.

A syringe pump system was used to measure the burst strength of a seal of an incision made in a section of uterine horn from a pig. The syringe pump (Model No. 22, Harvard Apparatus, Holliston, Mass.) was modified to be equipped with two 30 mL syringes, which were connected together through a "Y" junction. Water was pumped through a single piece of TYGON® R-36 tubing (0.6 cm diameter) and through a pressure gauge (Model PDG 5000 L, Omega Engineering, Stamford, Conn.).

An approximately 12.5 cm section of clean pig uterine horn, obtained from a local grocery store, was fitted on one end with a metal plug with a feed line fitting for water feed from the syringe pump and on the other end with a metal plug with a threaded hole which could be sealed with a machine screw. The plugs were held in place with nylon ties around the outside of the uterine horn. An incision was made through the uterine horn into the interior by puncturing with a BARD PARKER™ surgical blade handle 5 (obtained from BD Surgical Products, Franklin Lakes, N.J.), fitted with a #15 surgical blade. The incision on the outside of the uterine horn was wider than the scalpel blade (typically 4-5 mm) while the hole through the inside wall was about 3 mm (about equal to the blade). The uterine horn was filled with water containing a purple dye via the syringe pump until water began to leak from the open hole in the end plug and also from the scalpel puncture in the uterine horn. The pump was then turned off and the end plug was sealed with the machine screw. The scalpel incision site was blotted dry using a paper towel.

The dextran aldehyde solution (D10-50, 20 wt %) containing the thiol additive (see Table 7) and the multi-arm PEG amine solution (P8-10-1, 30 wt %) were prepared in water. The dextran aldehyde solution containing the thiol additive was allowed to remain at room temperature for two days prior to burst pressure testing. The two solutions were applied to the incision using a double barrel syringe (Mixpac Systems AG (Rotkreuz, Switzerland) fitted with a 8 step static mixer (Mixpac Systems AG). After the application, the adhesive was allowed to cure at room temperature for no longer than 2 min.

Burst pressure testing, also referred to herein as leak pressure testing, was done by pressurizing the sealed uterine horn with water from the syringe pump at a flow rate of 11 mL/min until the bioadhesive seal began to leak, at which point the pressure was recorded. Three measurements were made for each sample and the results, given as the average and standard deviation, are summarized in Table 7. Adhesive failure was attributed when the water leaked under the seal between the hydrogel and the tissue surface. Cohesive failure was attributed when the water penetrated and leaked through the hydrogel itself. Burst pressure testing was also done on the unsealed uterine horn and the leak pressure was less than 10 mm of mercury (Hg) (less than 1.3 kPa).

The results shown in Table 7 demonstrate that the hydrogels containing the thiol additives had good burst pressure and would be good candidates for use as bioadhesives.

TABLE 7

Burst Pressure Testing Results

| Example | Thiol Additive | Weight of Thiol Added to 10 g of Dextran Aldehyde solution (g) | Mol Ratio Thiol:Ald | Ave Burst Pressure, mmHg | Standard Deviation Burst Pressure, mmHg |
|---|---|---|---|---|---|
| 28 | thioglycerol | 0.2 | 0.13 | 130 | 56 |
| 29 | sodium 2-mercaptoethanesulfonate | 0.3 | 0.13 | 109 | 41 |

What is claimed is:

1. A kit for forming a hydrogel, said kit comprising:
   a) a first aqueous solution or dispersion comprising:
      (i) at least one oxidized polysaccharide containing aldehyde groups, having a weight-average molecular weight of about 1,000 to about 1,000,000 Daltons and having an equivalent weight per aldehyde group of about 65 to about 1,500 Daltons, said first aqueous solution or dispersion containing from about 5% to about 40% by weight of the oxidized polysaccharide; and
      (ii) at least one thiol additive, wherein the thiol additive is water-dispersible, contains only one reactive thiol (SH) group, does not contain any reactive carboxylic acid, primary amine or secondary amine groups, and has a molecular weight in the range of about 60 Daltons to about 40,000 Daltons, said first aqueous solution or dispersion containing about 0.1% to about 20% by weight of the thiol additive; and
   b) a second aqueous solution or dispersion comprising
      (i) at least one water-dispersible, multi-arm amine wherein at least three of the arms are terminated by at least one primary amine group, said multi-arm amine having a number-average molecular weight of about 440 to about 200,000 Daltons, said second aqueous solution or dispersion containing from about 5% to about 70% by weight of the multi-arm amine; or
      (ii) at least one a water-dispersible, multi-arm amine in the form of a neat liquid wherein at least three of the arms are terminated by at least one primary amine group, said multi-arm amine having a number-average molecular weight of about 440 to about 200,000 Daltons;

wherein the hydrogel has a decreased gelation time and a decreased degradation time compared to a hydrogel prepared with said oxidized polysaccharide and said water-dispersible, multi-arm amine in the absence of the thiol additive.

2. The kit of claim 1, wherein the thiol additive is selected from the group consisting of thioglycerol, methyl thioglycolate, 2-(2-methoxyethoxy)ethane thiol, and salts of 2-mercaptoethane sulfonate.

3. The kit of claim 1, wherein the oxidized polysaccharide is selected from the group consisting of oxidized derivatives of: dextran, carboxymethyldextran, starch, agar, cellulose, hydroxyethylcellulose, carboxymethylcellulose, pullulan, inulin, levan, and hyaluronic acid.

4. The kit of claim 1, wherein the water-dispersible, multi-arm amine is selected from the group consisting of water-dispersible multi-arm polyether amines, amino-terminated dendritic polyamidoamines, and multi-arm branched end amines.

5. The kit of claim 4, wherein the water-dispersible multi-arm polyether amines are selected from the group consisting of amino-terminated star polyethylene oxides, amino-terminated dendritic polyethylene oxides, amino-terminated comb polyethylene oxides, amino-terminated star polypropylene oxides, amino-terminated dendritic polypropylene oxides, amino-terminated comb polypropylene oxides, amino-terminated star polyethylene oxide-polypropylene oxide copolymers, amino-terminated dendritic polyethylene oxide-polypropylene oxide copolymers, amino-terminated comb polyethylene oxide-polypropylene oxide copolymers, and polyoxyalkylene triamines.

6. A hydrogel comprising the reaction product of:
   a) a first aqueous solution or dispersion comprising:
      (i) at least one oxidized polysaccharide containing aldehyde groups, having a weight-average molecular weight of about 1,000 to about 1,000,000 Daltons and having an equivalent weight per aldehyde group of about 65 to about 1,500 Daltons, said first aqueous solution or dispersion containing from about 5% to about 40% by weight of the oxidized polysaccharide; and
      (ii) at least one thiol additive, wherein the thiol additive is water-dispersible, contains only one reactive thiol (SH) group, does not contain any reactive carboxylic acid, primary amine or secondary amine groups, and has a molecular weight in the range of about 60 Daltons to about 40,000 Daltons, said first aqueous solution or dispersion containing about 0.1% to about 20% by weight of the thiol additive; and
   b) a second aqueous solution or dispersion comprising
      (i) at least one water-dispersible, multi-arm amine wherein at least three of the arms are terminated by at least one primary amine group, said multi-arm amine having a number-average molecular weight of about 440 to about 200,000 Daltons, said second aqueous solution or dispersion containing from about 5% to about 70% by weight of the multi-arm polyether amine; or
      (ii) at least one a water-dispersible, multi-arm amine in the form of a neat liquid wherein at least three of the arms are terminated by at least one primary amine group, said multi-arm amine having a number-average molecular weight of about 440 to about 200,000 Daltons;

wherein the hydrogel has a decreased gelation time and a decreased degradation time compared to a hydrogel prepared with said oxidized polysaccharide and said water-dispersible, multi-arm amine in the absence of the thiol additive.

7. The hydrogel of claim 6, wherein the thiol additive is selected from the group consisting of thioglycerol, methyl thioglycolate, 2-(2-methoxyethoxy)ethane thiol, and salts of 2-mercaptoethane sulfonate.

8. The hydrogel of claim 6, wherein the oxidized polysaccharide is selected from the group consisting of oxidized derivatives of: dextran, carboxymethyldextran, starch, agar, cellulose, hydroxyethylcellulose, carboxymethylcellulose, pullulan, insulin, levan, and hyaluronic acid.

9. The hydrogel of claim 6, wherein the water-dispersible, multi-arm amine is selected from the group consisting of water-dispersible multi-arm polyether amines, amino-terminated dendritic polyamidoamines, and multi-arm branched end amines.

10. The hydrogel of claim 9, wherein the water-dispersible multi-arm polyether amines are selected from the group consisting of amino-terminated star polyethylene oxides, amino-terminated dendritic polyethylene oxides, amino-terminated comb polyethylene oxides, amino-terminated star polypropylene oxides, amino-terminated dendritic polypropylene oxides, amino-terminated comb polypropylene oxides, amino-terminated star polyethylene oxide-polypropylene oxide copolymers, amino-terminated dendritic polyethylene oxide-polypropylene oxide copolymers, amino-terminated comb polyethylene oxide-polypropylene oxide copolymers, and polyoxyalkylene triamines.

11. A method for applying a hydrogel coating to an anatomical site on tissue of a living organism comprising:
  applying to the site
    a) a first aqueous solution or dispersion comprising:
      (i) at least one oxidized polysaccharide containing aldehyde groups, having a weight-average molecular weight of about 1,000 to about 1,000,000 Daltons and having an equivalent weight per aldehyde group of about 65 to about 1,500 Daltons, said first aqueous solution or dispersion containing from about 5% to about 40% by weight of the oxidized polysaccharide;
      and
      (ii) at least one thiol additive, wherein the thiol additive is water-dispersible, contains only one reactive thiol (SH) group, does not contain any reactive carboxylic acid, primary amine or secondary amine groups, and has a molecular weight in the range of about 60 Daltons to about 40,000 Daltons, said first aqueous solution or dispersion containing about 0.1% to about 20% by weight of the thiol additive;
      and
    b) a second aqueous solution or dispersion comprising
      (i) at least one water-dispersible, multi-arm amine wherein at least three of the arms are terminated by at least one primary amine group, said multi-arm amine having a number-average molecular weight of about 440 to about 200,000 Daltons, said second aqueous solution or dispersion containing from about 5% to about 70% by weight of the multi-arm amine; or
      (ii) at least one water-dispersible, multi-arm amine in the form of a neat liquid wherein at least three of the arms are terminated by at least one primary amine group, said multi-arm amine having a number-average molecular weight of about 440 to about 200,000 Daltons; wherein (a) and (b)(i) or (b) (ii) are applied to the site in any order, or (a) and (b) (i) or (b) (ii) are premixed and the resulting mixture is applied to the site before the mixture completely cures; and
  wherein the hydrogel coating has a decreased gelation time and a decreased degradation time compared to a hydrogel coating prepared with said oxidized polysaccharide and said water-dispersible, multi-arm amine, in the absence of the thiol additive.

12. The method of claim 11, wherein the thiol additive is selected from the group consisting of thioglycerol, methyl thioglycolate, 2-(2-methoxyethoxy)ethane thiol, and salts of 2-mercaptoethane sulfonate.

13. The method of claim 11, wherein the oxidized polysaccharide is selected from the group consisting of oxidized derivatives of: dextran, carboxymethyldextran, starch, agar, cellulose, hydroxyethylcellulose, carboxymethylcellulose, pullulan, inulin, levan, and hyaluronic acid.

14. The method of claim 11, wherein the water-dispersible, multi-arm amine is selected from the group consisting of water-dispersible multi-arm polyether amines, amino-terminated dendritic polyamidoamines, and multi-arm branched end amines.

15. The method of claim 14, wherein the water-dispersible multi-arm polyether amines are selected from the group consisting of amino-terminated star polyethylene oxides, amino-terminated dendritic polyethylene oxides, amino-terminated comb polyethylene oxides, amino-terminated star polypropylene oxides, amino-terminated dendritic polypropylene oxides, amino-terminated comb polypropylene oxides, amino-terminated star polyethylene oxide-polypropylene oxide copolymers, amino-terminated dendritic polyethylene oxide-polypropylene oxide copolymers, amino-terminated comb polyethylene oxide-polypropylene oxide copolymers, and polyoxyalkylene triamines.

16. A method of reducing the gelation time of a hydrogel comprising an oxidized polysaccharide and a water-dispersible, multi-arm amine, the method comprising:
  a) combining the oxidized polysaccharide containing aldehyde groups, having a weight-average molecular weight of about 1,000 to about 1,000,000 Daltons and having an equivalent weight per aldehyde group of about 65 to about 1,500 Daltons, said hydrogel containing from about 5% to about 40% by weight of the oxidized polysaccharide; with a thiol additive, wherein the thiol additive is water-dispersible, contains only one reactive thiol (SH) group, does not contain any reactive carboxylic acid, primary amine or secondary amine groups, and has a molecular weight in the range of about 60 Daltons to about 40,000 Daltons, said hydrogel containing about 0.1% to about 20% by weight of the thiol additive; to form a combination;
  b) allowing the combination to stand for a predetermined amount of time; and
  c) mixing the combination of oxidized polysaccharide and thiol additive with the water-dispersible, multi-arm amine to form the hydrogel;
  d) wherein the hydrogel has a decreased gelation time compared to a hydrogel prepared with said oxidized polysaccharide and said water-dispersible, multi-arm amine in the absence of the thiol additive.

17. The method of claim 16 wherein the predetermined amount of time is at least two hours.

18. A method of reducing the degradation time of a hydrogel comprising an oxidized polysaccharide and a water-dispersible, multi-arm amine, the method comprising:

a) combining the oxidized polysaccharide containing aldehyde groups, having a weight-average molecular weight of about 1,000 to about 1,000,000 Daltons and having an equivalent weight per aldehyde group of about 65 to about 1,500 Daltons, said hydrogel containing from about 5% to about 40% by weight of the oxidized polysaccharide; with a thiol additive, wherein the thiol additive is water-dispersible, contains only one reactive thiol (SH) group, does not contain any reactive carboxylic acid, primary amine or secondary amine groups, and has a molecular weight in the range of about 60 Daltons to about 40,000 Daltons, said hydrogel containing about 0.1% to about 20% by weight of the thiol additive; to form a combination;
b) allowing the combination to stand for a predetermined amount of time; and
c) mixing the combination of oxidized polysaccharide and thiol additive with the water-dispersible, multi-arm amine to form the hydrogel;
d) wherein the hydrogel has a decreased degradation time compared to a hydrogel prepared with said oxidized polysaccharide and said water-dispersible, multi-arm amine in the absence of the thiol additive.

19. The method of claim 18 wherein the predetermined amount of time is at least two hours.

20. An aqueous solution or dispersion comprising:
a) at least one oxidized polysaccharide containing aldehyde groups, having a weight-average molecular weight of about 1,000 to about 1,000,000 Daltons and having an equivalent weight per aldehyde group of about 65 to about 1,500 Daltons, and
b) at least one thiol additive, wherein the thiol additive is water-dispersible, contains only one reactive thiol (SH) group, does not contain any reactive carboxylic acid, primary amine or secondary amine groups, and has a molecular weight in the range of about 60 Daltons to about 40,000 Daltons.

* * * * *